(12) United States Patent
Tsuganezawa et al.

(10) Patent No.: US 6,335,175 B1
(45) Date of Patent: Jan. 1, 2002

(54) ANTI-HUMAN PRE-B CELL RECEPTOR ANTIBODY

(75) Inventors: Keiko Tsuganezawa, Kanagawa; Hajime Karasuyama, 4-29, Nukuikitamachi 2-chome, Koganei-shi, Tokyo 184-0015, both of (JP)

(73) Assignees: Sumitomo Electric Industries, Ltd., Osaka; Hajime Karasuyama, Tokyo, both of (JP)

( * ) Notice: Subject to any disclaimer, the term of this patent is extended or adjusted under 35 U.S.C. 154(b) by 0 days.

(21) Appl. No.: 09/494,252

(22) Filed: Jan. 31, 2000

Related U.S. Application Data

(63) Continuation-in-part of application No. PCT/JP98/03384, filed on Jul. 29, 1998.

(30) Foreign Application Priority Data

Jul. 29, 1997 (JP) .............................................. 9-202684
Oct. 29, 1997 (JP) .............................................. 9-296090

(51) Int. Cl.$^7$ .................... G01N 33/574; A61K 39/395; C12P 21/08; C07K 15/00
(52) U.S. Cl. ................ 435/7.23; 424/138.1; 424/130.1; 530/388.1; 530/389.1
(58) Field of Search ........................... 530/388.1, 389.1; 424/130.1, 138.1; 435/7.23

(56) References Cited

U.S. PATENT DOCUMENTS 5,182,205 A * 1/1993 Bauer et al. ............. 435/240.2

FOREIGN PATENT DOCUMENTS

JP 60-42400 3/1985

OTHER PUBLICATIONS

Alberts et al., Molecular Biology of the Cell, 1983, pp. 965–966.*

Calbiochem Catalogue, 1994/1995, p. 299.*

"Expression of Surrogate Light Chain Receptors Is Restricted to a Late Stage in Pre–B Cell Differentiation", by Lassoued et al., *Cell*, vol. 73, Apr. 9, 1993, pp. 73–86.

"Discrete Early Pro–B and Pre–B Stages in Normal Human Bone Marrow as Defined by Surface Pseudo–Light Chain Expression", by Guelpa–Fonlupt et al., *Eur. J. Immunol.*, vol. 24, 1994, pp. 257–264.

"Cell Surface Expression of Surrogate Light Chain ($\psi$L) in the Absence of $\mu$ on Human Pro–B Cell Lines and Normal Pro–B Cells", by Meffre et al., *Eur. J. Immunol.*, vol. 26, 1996, pp. 2172–2180.

"A Novel Anti–Vpre–B Antibody Identifies Immunoglobulin–Surrogate Receptors on the Surface of Human Pro–B Cells", by Sanz et al., *J. Exp. Med.*, vol. 183, Jun. 1996, pp. 2693–2698.

"The Recombinant Immunotoxin Anti–Tac (Fv)–Pseudomonas Exotoxin 40 is Cytotoxic Toward Peripheral Blood Malignant Cells from Patients with Adult T–cell Leukemia", by Kreitman et al., *Proc. Nat. Acad. Sci. USA*, vol. 87, Nov. 1990 pp. 8291–8295.

"The Proteins Encoded by the $V_{preB}$ and $\lambda_5$ Pre–B Cell–specific Genes Can Associate with Each Other and With $\mu$ Heavy Chain", by Karasuyama et al., *J. Exp. Med.*, vol. 172, Sep. 1990, pp. 969–972.

"Growth Autonomy and Tumorigenicity of Interleukin 6–Dependent B Cells Transfected with Interleukin 6 cDNA", by Tohyama et al., *J. Exp. Med.*, vol. 171, Feb. 1990, pp. 389–400.

"Antibody Prurification Using Caprylic Acid", by Russ et al., *Storing and purifying Antibodies*, Chapt. 8, pp. 300–301 (1983).

"A New Mouse Myeloma Cell Line That Has Lost Immunoglobulin Expression But Permits the Construction of Antibody–Secreting Hybrid Cell Lines", by Kearney et al., *The Journal of Immunology*, vol. 123, No. 4, Oct. 1979, pp. 1548–1550.

* cited by examiner

*Primary Examiner*—Yvonne Eyler
*Assistant Examiner*—Janet L. Andres
(74) *Attorney, Agent, or Firm*—McDermott, Will & Emery

(57) ABSTRACT

The present invention provides an antibody which recognizes a human pre-B cell receptor and does not recognize a human pro-B cell. The invention also provides an antibody which reacts with a VpreB molecule, one of the constituents of an SL chain of a human pre-B cell receptor expressed on the membrane surface of a human pre-B cell, or a VpreB molecule expressed within a human pro-B cell, but does not react with a $\lambda 5$ molecule of the surrogate light chain, and whose reactivity is such that a human pre-B cell or a human pro-B cell reacted with the antibody can be detected microscopically. The invention further provides a method for diagnosing which differentiation stage of B cells acute lymphoblastic leukemia in childhood stems from, by using an antibody which recognizes a human pre-B cell receptor, and does not recognize a human pro-B cell, an antibody which recognizes a VpreB molecule of a surrogate light chain constituting a human pre-B cell receptor, an antibody which recognizes a $\lambda 5$ molecule of the surrogate light chain constituting a human pre-B cell receptor, and an antibody which recognizes a B cell.

3 Claims, 12 Drawing Sheets

ANTI-HUMAN PRE-B CELL RECEPTOR ANTIBODY

RELATED APPLICATION

This is a continuation-in-part application of application Ser. No. PCT/JP98/03384 filed on Jul. 29, 1998, now pending, which in turn claims the benefit of Japanese Patent Application No. 202684/1997, filed Jul. 29, 1997, and Japanese Patent Application No. 296090/1997, filed Oct. 29, 1997, the disclosures of which Applications are incorporated by reference herein. The benefit of the filing and priority dates of the International and Japanese Applications is respectfully requested.

BACKGROUND OF THE INVENTION

1. Field of the Invention

This invention relates to an antibody which recognizes a human pre-B cell receptor. The invention also relates to an antibody which reacts with a VpreB molecule of a surrogate light chain of a human pre-B cell receptor expressed on the surface of a human pre-B cell, VpreB in the cytoplasm of the pre-B cell, and a VpreB molecule expressed in the cytoplasm a human pro-B cell; or an active fragment of this antibody. The invention further relates to a method of detecting a human pro-B cell and a human pre-B cell by the above-mentioned antibody or its active fragment with the use of a saponin buffer. The antibody of the present invention can be applied to the diagnosis of acute lymphoblastic leukemia.

2. Related Background Art

B cell is known to differentiate from a hematopoietic stem cell of bone marrow into a plasma cell through the stages of pro-B cell, pre-B cell, immature B cell, and mature B cell.

On the surface of a B cell, immunoglobulin is expressed (may be referred to hereinafter as Ig) as an antigen-recognizing receptor. The antigen-recognizing receptor is composed of two types of polypeptides, i.e., a heavy chain and a light chain. Its composition varies as the B cell is differentiated.

Differentiation of B cell and its antigen-recognizing receptor will be described with a mouse taken as an example.

In pro-B cell, it is known that a surrogate light chain (SL chain), which is composed of two associated polypeptides called $\lambda 5$ and vpreB, is associated with a heavy chain (H chain) called a surrogate heavy chain (SH chain), and the associated pair is expressed on the cell surface. The surrogate light chain is so called, because the $\lambda 5$ molecule (may be referred to hereinafter as $\lambda 5$) and the VpreB molecule (may be referred to hereinafter as VpreB) are associated together to substitute for an ordinary light chain (L chain). $\lambda 5$ corresponds to the constant region of a light chain, while VpreB corresponds to the variable region of the light chain.

With regard to pre-B cell, a pre-B cell receptor is known to be expressed on the surface of the cell. In the pre-B cell receptor, a surrogate light chain (SL chain), which is composed of two associated polypeptides called $\lambda 5$ and VpreB, is associated with a heavy chain (H chain) called $\mu$ chain.

In an immature B cell and a mature B cell, a B cell receptor composed of an ordinary L chain bound to $\mu$ chain is expressed as an antigen-recognizing receptor.

As will be seen from the foregoing description, $\lambda 5$ and VpreB are expressed only in pro-B cell and pre-B cell.

With a human pre-B cell receptor, similar findings have been reported.

The following are known as antibodies which react with the human pre-B cell receptor. Their reactivity, etc. are shown in Table 1.

① Anti-human pre-B cell receptor antibodies: SLC1, SLC2, SLC3, SLC4 (Cell, Vol. 73, 73–86, 1993)

② Anti-human pre-B cell receptor antibody: 9C2 (Eur. J. Immunolo., Vol. 24, 257–264, 1994)

③ Anti-human VpreB antibodies: 3C7, 6F6 (Eur. J. Immunolo., Vol. 26, 2172–2180, 1996)

④ Anti-human VpreB antibodies: B-MAD176, B-MAD688, B-MAD792, B-MAD1112 (J. Exp. Med., Vol. 183, 2693–2698, 1996)

TABLE 1

| Antibody | Immunogen | Cell surface staining (FACS) | | Reaction site | Immunoprecipitation | Isotype |
| | | Pro-B cell | Pre-B cell | | | |
| --- | --- | --- | --- | --- | --- | --- |
| SLC1 | Pre-B cell receptor | Negative | Positive | $\lambda 5$ | No data | IgG |
| SLC2 | Pre-B cell receptor | Negative | Positive | $\lambda 5$ | No data | IgM |
| SLC3 | Pre-B cell receptor | Negative | Positive | $\lambda 5$ | No data | IgM |
| SLC4 | Pre-B cell receptor | Negative | Positive | $\lambda 5$ | No data | IgG |
| 9C2 | Part of synthetic VpreB molecule | Very weakly positive | Positive | VpreB | No data | IgM |
| 3C7 | Recombinant VpreB | Positive | Very weakly positive | VpreB | No data | IgM |
| 6F6 | Recombinant VpreB | Positive | Very weakly positive | VpreB | No data | IgM |
| B-MAD176 | Recombinant VpreB | Negative | Positive | No data | No data | IgM |
| B-MAD688 | Recombinant VpreB | Positive | Positive | VpreB | SH chain (only when formed as complex with SL chain) | IgM |
| B-MAD792 | Recombinant VpreB | Negative | Positive | No data | No data | IgM |
| B-MAD1112 | Recombinant VpreB | Positive depending on cell strain | Positive | VpreB | No data | IgM |

SUMMARY OF THE INVENTION

An abnormality in B cell differentiation causes leukemia. Knowing at which stage of differentiation B cell multiplied abnormally is important in treating leukemia. In acute lymphoblastic leukemia in childhood, in particular, abnormal proliferation of pro-B cell or pre-B cell may be a frequent cause. Currently, B cell surface markers generally used in diagnosis are CD10, CD19, CD20, and CD21. Attempts have been made to react any of these antibodies with B cell and to determine by the results which stage the B cell is at. However, CD19, CD20, and CD21 also react with an immature B cell or a mature B cell, while CD10 also reacts with a T cell or an epithelial cell. These antibodies, therefore, were unable to detect only a human pro-B cell or a human pre-B cell specifically.

The present invention aims to provide an antibody which recognizes a human pre-B cell receptor, and which does not recognize a human pro-B cell, thereby making it possible to distinguish between human pre-B cell and human pro-B cell and detect human pre-B cell or human pro-B cell specifically.

In the field of clinical diagnosis, microscopic observation of a cell is made. Compared with other methods, this is the most convenient and fastest method that requires the smallest space for installation of equipment. If staining of the cell is very weak, however, it cannot be observed under a microscope, although it can be detected by a highly accurate detection method such as FACS. All the antibodies against a human pre-B cell receptor enumerated earlier as above-mentioned ① to ④, especially the antibodies against VpreB, only gave the results with FACS. That is, it has not been shown whether they have reactivity enough to stain the antibody-reacted cell so as to be observable microscopically. Also, it has been shown that reactivity with a human pro-B cell is only reactivity on the surface of the cell, and intracellular staining has not been shown.

It is another object of the present invention to provide an antibody which reacts specifically with a human pre-B cell and a human pro-B cell, and which can immunostain a human pre-B cell expressing a human pre-B cell receptor on the surface and a human pro-B cell expressing a VpreB molecule intracellularly so that only the immunostained cell can be observed microscopically.

To attain this object, the present invention provides an antibody which recognizes a human pre-B cell receptor and does not recognize a human pro-B cell. The antibodies of this invention are an antibody which recognizes a stereo-structure formed by the μ chain, λ5 and VpreB of a human pre-B cell, and an antibody which reacts with a VpreB molecule, one of the constituents of the SL chain of a human pre-B cell receptor expressed on the surface of a human pre-B cell, or reacts with a VpreB molecule expressed in the cytoplasm of a human pro-B cell, but does not react with a λ5 molecule, and whose reactivity is such that the human pre-B cell or human pro-B cell reacted with the antibody can be detected microscopically.

The invention also provides an anti-human pre-B cell receptor antibody as claimed in claim 1 which is a monoclonal antibody produced by hybridoma HSL2 (originally deposited on Oct. 16, 1997 under acceptance No. FERM-P16476 with National Institute of Bioscience and Human Technology (NIBHT), Agency of Industrial Science and Technology, Ministry of Industrial Trade and Industry, 1–3, Higashi 1-chome, Tsukuba-shi, Ibaraki-ken, Japan; and transferred on May 25, 1998 under acceptance No. FERM-BP6378 to NIBHT, the international deposition organization), or an active fragment of the monoclonal antibody.

The invention also provides an anti-human pre-B cell antibody or its active fragment which is a monoclonal antibody produced by hybridoma HSL96 (originally deposited with NIBHT on May 30, 1997 under acceptance No. FERM-P16251; and transferred on May 25, 1998 under acceptance No. FERM-BP6375 to NIBHT, the international deposition organization), or an active fragment of the monoclonal antibody.

The invention also provides a method for detecting a human pro-B cell, which comprises immunostaining a human pro-B cell in a sample with the use of the antibody or its active fragment to detect the human pro-B cell; characterized by using saponin buffer when immunostaining a VpreB molecule in the human pro-B cell.

The invention also provides a diagnostic agent for diagnosing which differentiation stage of B cell acute lymphoblastic leukemia in childhood results from; characterized by containing at least (1) an antibody which recognizes a human pre-B cell receptor and does not recognize a human pro-B cell, (2) an antibody which recognizes a VpreB molecule of a surrogate light chain constituting a human pre-B cell receptor, (3) an antibody which recognizes a λ5 molecule of a surrogate light chain constituting a human pre-B cell receptor, and (4) an antibody which recognizes a B cell.

The invention also provides a method for diagnosing which differentiation stage of B cell acute lymphoblastic leukemia in childhood results from, by using an antibody which recognizes a human pre-B cell receptor, and does not recognize a human pro-B cell, an antibody which recognizes a VpreB molecule of a surrogate light chain constituting a human pre-B cell receptor, an antibody which recognizes a λ5 molecule of a surrogate light chain constituting a human pre-B cell receptor, and an antibody which recognizes a B cell.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 3 is a view showing the arrangement of FIGS. 3A to 3C;

FIG. 4 is a view showing the arrangement of FIGS. 4A to 4H;

FIG. 5 is a view showing the arrangement of FIGS. 5A to 5H;

FIG. 6 is a view showing the arrangement of FIGS. 6A to 6D;

DESCRIPTION OF THE PREFERRED EMBODIMENTS

1. Active Fragment of Antibody

Figure 1:
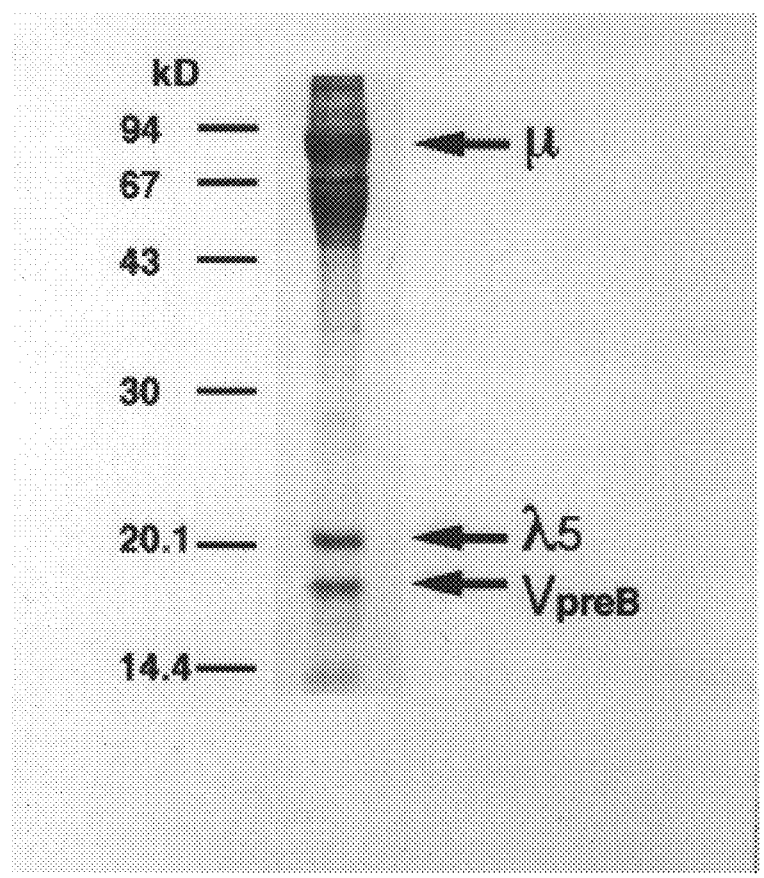
FIG. 1 is an electrophoretic photograph of a chimeric pre-B cell receptor (mouse μ chain/human λ5/human VpreB) used as an immunogen for preparing antibodies of the present invention.

In the present invention, an antibody embraces its active fragment as well. The active fragment refers to a fragment of an antibody having antigen-antibody reaction activity. Specifically, F(ab')$_2$, Fab', Fab, and Fv are exemplified.

For example, when the antibody of the invention is digested with pepsin, F(ab')$_2$ is obtained; when it is digested with papain, Fab is obtained. By reducing F(ab')$_2$ with a reagent such as 2-mercaptoethanol, and by alkylating with monoiodoacetic acid, Fab' is obtained. Fv is a monovalent antibody activity fragment comprising a heavy chain variable region and a light chain variable region which are linked together by a linker.

By maintaining these active fragments, and replacing other portion by fragments of an antibody originated from other animal, a chimeric antibody is obtained. In the present specification, the "chimeric antibody" refers to an antibody whose variable region or antigen-binding domain and constant region or effector domain are composed of immunoglobulin fragments belonging to genetically different species. For example, a variable (V) region fragment of a mouse monoclonal antibody can be coupled to a human constant (C) region fragment, e.g., γ1 or γ4.

2. Genetic Engineering Method for Production

The antibody of the present invention can also be obtained with the use of a genetic engineering method. For example, mRNA is collected from spleen cells or lymphocytes of an animal immunized with an associated pair of the μ chain and SL chain of a pre-B cell receptor, or from a hybridoma which produces a monoclonal antibody of the present invention. Based on this mRNA, a cDNA library is prepared. Then, antibodies are expressed by use of the cDNA library. Clones which produce antibodies reactive with the antigen are obtained from the cDNA library by screening. The resulting clones are cultured, and the desired antibody can be purified from a culture mixture by a combination of methods, such as salting-out, ion exchange chromatography, and affinity chromatography.

3. Method of Detection

Detection of a human pre-B cell or pre-B cell receptor using the antibody of the present invention can be achieved by any of ELISA, FACS, immunoprecipitation, and microscopic observation.

The FACS method or microscopic observation, in particular, can not only detect pre-B cell receptor or VpreB molecule on the cell surface, but also detect intracellular VpreB molecule or cell having this molecule inside, by using a saponin buffer when mixing the antibody with a sample for their reaction and staining the intracellular VpreB molecule as well.

4. Use as an Immunotoxin

Preparation of an immunotoxin having a toxin bound to an antibody can be realized by the method described, for example, in Proc. Natl. Acad. Sci. USA, Vol. 87 (1990), pp. 8291–8295. Application of this method to the antibody of the present invention makes it possible to bind a toxin thereto and to prepare an immunotoxin. When this immunotoxin is administered to a patient with leukemia due to pre-B cells, its toxin can act selectively on pre-B cells proliferated in the patient's body, and thus can eradicate these cells and treat leukemia due to the cells. Examples of this toxin are exotoxin and diphtheria toxin.

5. Use as a Complex

The antibody or its active fragment of the present invention can be used alone, but can be used as a novel complex when joined to a substance, such as albumin or polyethylene glycol, when necessary. Such a complex generally is not decomposed, but shows its effect maximally, for a long time in vivo. Generally, the active fragment can be easily bound to albumin or the like, if a divalent reactive reagent such as SPDP (a product of Sigma or Amersham Pharmacia).

EXAMPLES

Examples of the present invention will now be offered for a more specific explanation of the invention. However, the invention is not restricted thereto, and the animals to be immunized, the cell strain used, and the labeling antibody may be others, depending on the purpose to be attained.

Example 1

Preparation of Antibody (1)

1. Preparation of Antigen
   1) Construction of Antigen Gene Recombinant
   (1) Preparation of λ5 Gene and VpreB Gene
   A human λ5 gene and a human VpreB gene were prepared by preparing mRNA from the human pre-B cell Nalm6 by the customary method, and performing RT-PCR of the mRNA using the primers indicated below. The resulting mRNA was sequenced, and was confirmed to have the base sequence of the human λ5 gene and the human VpreB gene.
   λ5 primers:
   5' primer 5'-GGA ACT CGA GCC ACA AGG ACC TCT GAC CCT-3' (SEQ ID NO:1)
   3' primer 5'-GGA AGC GGC CGC AGG CCT TTG GGT GGG GTC GG-3' (SEQ ID NO:2)
   VpreB primers:
   5' primer 5'-GGA ACT CGA GGG AGT CAG AGC TCT GCA TGT-3' (SEQ ID NO:3)
   3' primer 5'-GGA AGC GGC CGC AGG GGA TGC GTG CCT CTG CT-3' (SEQ ID NO:4)
   (2) Insertion into Vector
   The λ5 gene and the VpreB gene prepared in (1) were inserted by the customary method into a mammalian expression vector BCMGSHyg having a promoter of cytomegalovirus and an enhancer of μ chain of immunoglobulin (this expression vector was produced by the method described in J. Exp. Med., Vol. 172, 969–972).
   (3) Preparation of Transformant
   The vector prepared in (2) was introduced by electroporation into a host Ltk⁻ (mouse μ chain) which expresses mouse μ chain (for this method, see J. Exp. Med., Vol. 172, 969–972) to prepare a transformant Ltk⁻ (mouse μ chain/human λ5/human VpreB) which expresses and secretes a chimeric pre-B cell receptor (mouse μ chain/human λ5/human VpreB).
   (4) Screening of Transformant
   ① The transformant Ltk⁻ (mouse μ chain/human λ5/human VpreB) was cultured in 96-well plates at 37° C. under 5% $CO_2$ using a 10% FCS-RPMI1640 medium containing 0.2 mg/ml of hygromycin and G418.
   ② The culture supernatant was measured by ELISA under the condition 1 indicated below. In about 600 wells of 1,200 wells, colonies appeared. Of these wells, 16 wells with highest absorbance at 405 nm were selected as positive.
   ELISA conditions 1
   Coating of 96-well plates: 96-well plates were coated with goat anti-mouse IgM (10 μg/ml).
   Sample: Culture supernatant of transformant Ltk⁻ (mouse μ chain/human λ5/human VpreB)
   Antibody for detection: Alkaline phosphatase-labeled goat anti-mouse IgM (a product of Southern Biotechnology Associates diluted 1:300)
   Substrate: PNPP (p-nitrophenyl phosphate, Sigma).
   ③ ELISA of aforementioned item ② was repeated several times, and positive strains were cloned using limiting dilution. A positive strain showing high expression of pre-B cell receptor (mouse μ chain/human λ5/human VpreB) was selected. This positive strain was named Ltk⁻ 17–72.

2) Large Scale Culture of Antigen Protein

The transformant Ltk⁻ 17–72 obtained above was cultured at 37° C. in a 5% FCS-RPMI1640 medium in a plurality of 1-liter roller bottles. The medium (200 ml) was poured per the roller bottle, and the Ltk⁻ 17–72 was cultured for 2 weeks. After 2-week culture, the concentration of the pre-B cell receptor (mouse μ chain/human λ5/human VpreB) in the medium was measured under the ELISA condition 1 described above. The said concentration was found to be about 5 ng/ml.

3) Purification of Antigen (1) Concentration

The culture supernatant of the aforementioned item 2) was collected in an amount of 2 liters, and concentrated about 10-fold by means of a concentrator (MINITAN, a registered trademark, available from Millipore).

(2) Purification

① A rat anti-mouse μ chain antibody was conjugated to beads (CNBr activated Sepharose 4B, Pharmacia), and the beads were packed into a column.

② The concentrated culture supernatant was circulated through this column for 2 weeks to conjugate the pre-B cell receptor (mouse μ chain/human λ5/human VpreB) which are in the culture supernatant as an antigen protein to the beads, so as to prepare an antigen-bead conjugate.

The foregoing concentration and purification were performed for the culture supernatant in a total amount of about 20 liters to prepare an antigen protein-bead conjugate having 50 μg of the antigen protein conjugated to 500 μl of the antigen beads (recovery of the antigen protein in the culture medium was 50%).

2. Immunization

The resulting antigen protein-bead conjugate was inoculated subcutaneously to the root of the limbs of a female BALB/c mouse for immunization with 1 μg/10 μl beads per animal. For second and later immunizations, a suspension of the antigen protein-bead conjugate in PBS was inoculated a total of 7 times every 8 days in an amount of 1 μg/10 μl beads per animal. Then, 8 weeks apart, an antigen protein solution (antigen protein amount 30 μg) eluted from the antigen protein-bead conjugate was intravenously injected to the tail for boostering.

FIG. 1 shows the results of SDS-PAGE electrophoresis of the antigen protein solution (a solution dissolved from the antigen protein-bead conjugate with 0.1 M glycine, pH 2.7). The electrophoresis showed bands for μ chain, λ5, and VpreB, confirming the antigen protein to be a secretor pre-B cell receptor (mouse μ chain/human λ5/human VpreB) composed of these constituents.

3. Preparation of Monoclonal Antibody

1) Preparation of Hybridoma

Three days after boostering, $2.2 \times 10^8$ spleen cells were taken from the spleen of the immunized mouse, and subjected to polyethylene glycol (Boehringer) cell fusion with mouse myeloma cells PAI at a ratio of 4:1. Thus, obtained hybridomas were distributed at ten 96-well plates, and cultured in 20% FCS-IMDM (Gibco) incorporating a 1:100 dilution of HAT (Boehringer) and a 1:500 dilution of IL-6 (a culture supernatant of transformant X63BCMGNeo (for its production method, see J. Exp. Med., Vol. 171, 389–400)).

2) Screening (1) ELISA

The hybridomas were cultured for about 2 weeks. In about 260 wells of 960 wells (10 plates), colonies were formed. Culture supernatants of the hybridomas that formed colonies were screened by ELISA under the following condition 2:

ELISA condition 2

① Coating of 96-well plates: Four types of antibodies shown below were coated on 96-well plates. Each antibody used for coating had a concentration of 10 μg/ml, and was added in an amount of 50 μl to each well of the plate, and the plates were allowed to stand overnight at 4° C. Then, the plates were washed with 0.05% Tween 20-PBS, whereafter 200 μl of 4% BSA-0.2% Tween 20-PBS was added as a blocking solution to each well, and the plates were allowed to stand for 1 hour at 4° C.

A: Coated with goat anti-mouse μ chain antibody (Southern Biotechnology Associates) for blocking, and then coated with a 10-fold concentrate of the culture supernatant of Ltk⁻17–72.

B: Coated with goat anti-mouse μ chain antibody (described above).

C: Coated with human IgM (μ chain and λ chain) (Southern Biotechnology Associates).

D: Coated with human IgM (μ chain and κ chain) (Southern Biotechnology Associates).

② Antigen-antibody reaction: After each plate was washed with 0.05% Tween 20-PBS, 30 μl of 4% BSA-0.2% Tween 20-PBS was added as a diluent to each well. Further, 30 μl of each culture supernatant of the above hybridoma was added to each well, and these materials were mixed. The mixture was allowed to stand for 2 hours at room temperature to carry out the antigen-antibody reaction.

③ Color development reaction: After the antigen-antibody reaction, each plate was washed with 0.05% Tween 20-PBS. Then, 100 μl of alkaline phosphatase-labeled goat anti-mouse IgG antibody (a product of Southern Biotechnology Associates diluted at ratio of 1:500) was added to each well as a detecting antibody, and the plate was allowed to stand for 1 hour at room temperature. After each plate was washed with 0.05% Tween 20-PBS, 100 μl of PNPP was added to each well as a substrate. The plate was allowed to stand for 30 minutes at room temperature to cause color development.

④ Then, the absorbance of the mixture at 405 nm was measured.

The samples presenting high absorbance at 405 nm were evaluated as positive. Those hybridomas producing culture supernatants which became positive on the coating A and negative on the coating B, C and D were selected. As a result, hybridomas of 14 wells among the hybridomas of the 260 wells that formed colonies were selected.

(2) Staining of Cell Surface

From the 14 hybridoma clones selected as positive strains, it was attempted to select clones which produce positive results upon reaction with a pre-B cell receptor expressed on the cell surface of the human pre-B leukemia cell line Nalm6. For this purpose, staining of the cell surface was performed.

Specifically, $1 \times 10^6$ Nalm6 cells were put into each well of a 96-well plate. To each well, 50 μl of a culture supernatant of each clone was added, and the mixture was reacted for 30 minutes at room temperature. Then, 100 μl of PE-labeled goat anti-mouse κ chain antibody was added as a secondary antibody to each well.

This sample was measured with FACS Calibur (Becton Dickinson).

As controls for cross-reactivity, cell surface staining was similarly performed for mature B cells Daudi and LBW-4, and measurements were made with FACS Calibur.

Of the 14 clones, 4 clones proved positive with Nalm6, and negative with Daudi and LBW-4.

(3) Immunoprecipitation

A culture supernatant (1 ml) of each of the 4 clones was mixed overnight with 20 μl of protein G Sepharose (Pharmacia) at a ratio of 50% V/V at 4° C.

The mixture was centrifuged for 5 minutes at 10,000 rpm to separate the antibody-bound protein G Sepharose.

The protein G Sepharose was washed with a solvent (1% NP-40, 150 mM NaCl).

Pre-B cells Nalm6 ($1 \times 10^5$) intracellularly labeled with isotope $^{35}$S methionine/cysteine and a solvent (1% NP-40, 150 mM NaCl) were mixed to obtain a cell solution.

The antibody-bound protein G Sepharose was suspended in the cell solution, and mixed for 2 hours.

The mixture was centrifuged for 5 minutes at 10,000 rpm to separate an immunoprecipitate (Nalm6-derived protein bound to the protein G Sepharose).

Washing of the immunoprecipitate with about 1 ml of a washing solution (1% NP-40, 650 mM NaCl) was repeated 4 times to obtain the immunoprecipitate as a sample for electrophoresis.

Figure 2:
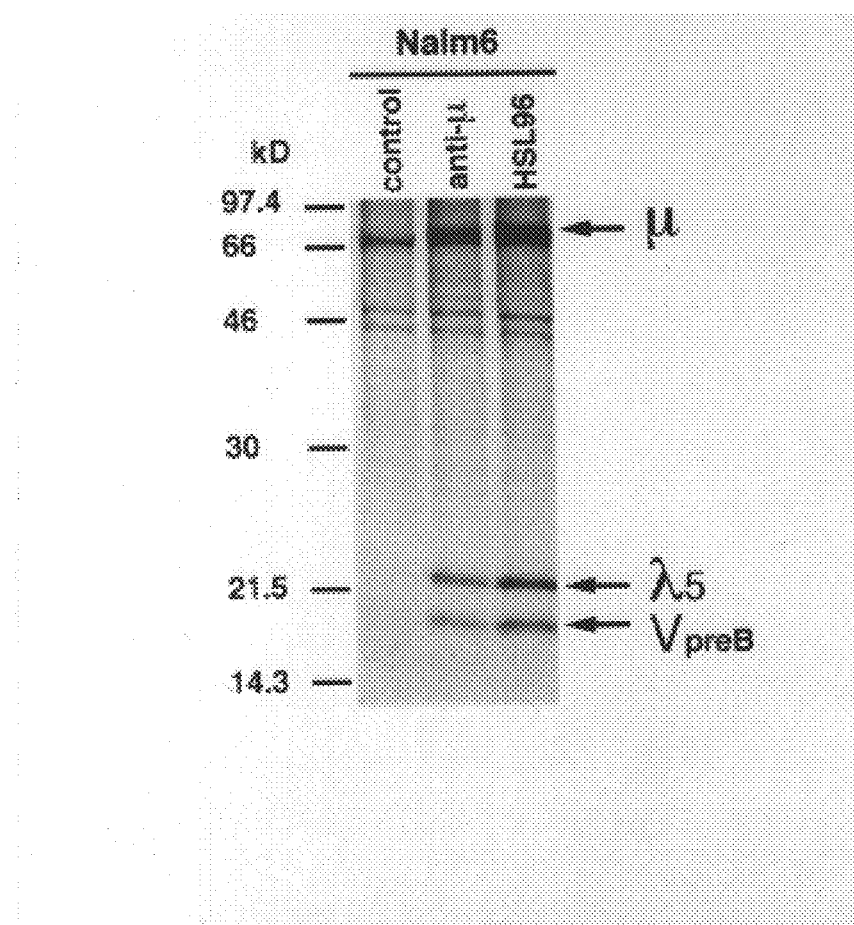
FIG. 2 is an electrophoretic photograph showing the results of electrophoresis of an immunoprecipitate obtained by using the supernatant of a culture of a hybridoma selected by screening with immunoprecipitation.

The immunoprecipitates were reduced for 5 minutes at 95° C. in the presence of 2-mercaptoethanol, and electrophoresed on 13% sodium dodecyl sulfate (SDS) polyacrylamide gel. Three bands of a pre-B cell receptor (human μ/human λ5/human VpreB) were confirmed in 1 of the 4 clones. The results of electrophoresis of this clone are shown in FIG. 2. For comparison, a culture supernatant (control) containing mouse IgG and a culture supernatant containing anti-human μ chain antibody were used.

3) Cloning

The hybridoma of the above finally left clone was cloned by limiting dilution to a level of one cell/well in a 96-well plate, followed by culturing for 10 days. Ten colonies giving one colony/well were selected, and subjected to ELISA under the ELISA condition 2 to measure the absorbance on the coating A. A hybridoma showing the highest absorbance was named HSL96, and deposited May 30, 1997 with National Institute of Bioscience and Human Technology, Agency of Industrial Science and Technology (acceptance No. FERM-P16251). At the same institute, the international deposition organization, this hybridoma was transferred on May 25, 1998 to deposition based on the Budapest Treaty (acceptance No. FERM BP-6375). An antibody produced by the hybridoma HSL96 is called HSL96 antibody.

4. Mass Production of Monoclonal Antibody

Pristane (0.5 ml) was intraperitoneally injected into a 7-week-old ICRnu/nu mouse (Charles Reever), and 5 days later, $1 \times 10^7$ hybridoma HSL96 cells were injected into each mouse. About 2 weeks later, ascites was recovered, and purified in accordance with the caprylic acid method (the method described in Antibodies: A Laboratory Manual, Chapter 8, page 300, 1988, Cold Spring Harbor Laboratory) to obtain a monoclonal antibody. The subclass of this antibody was confirmed to be IgG$_1$κ with the use of a monoclonal mouse Ig isotyping kit (Farmingene).

Example 2

Preparation of Antibody (2)

Another monoclonal antibody which recognizes a human pre-B cell receptor was prepared in the same manner as in Example 1.

Colonies developed in about 600 wells of 768 wells (8 plates) containing the hybridomas subjected to ELISA during screening at the time of hybridoma preparation. Screening by ELISA resulted in the selection of hybridomas of 28 wells among the hybridomas of the 600 wells that formed colonies.

The supernatants of the 28 hybridoma clones selected as positive strains were each reacted with a pre-B cell receptor expressed on the cell surface of human pre-B leukemia cell strain Nalm6, and cell surface staining was performed. Measurement with FACS Calibur (Becton Dickinson) showed 7 of the 28 clones to be positive with Nalm6, and negative with Daudi and LBW-4.

In the same manner as in cell surface staining, cytoplasmic staining was performed using 0.1% BSA-0.05% saponin-10 mM Hepes (pH 7.3)-PBS as a buffer for suspending the cells and the antibody. Measurement with FACS Calibur showed 1 of the 7 clones to be positive with Nalm6, and negative with Daudi and LBW-4.

The hybridoma of the above finally left one clone was cloned by limiting dilution to a level of one cell/well in a 96-well plate, followed by culturing for 10 days. Ten colonies giving one colony/well were selected, and subjected to ELISA under the ELISA condition 2 to measure the absorbance on the coating A. The hybridoma showing the highest absorbance was named HSL2, and originally deposited with National Institute of Bioscience and Human Technology, Agency of Industrial Science and Technology (1–3, Higashi 1-chome, Tsukuba-shi, Ibaraki-ken, Japan) on Oct. 16, 1997 under the acceptance No. FERM-P16476. Further, this hybridoma was transferred to the same institute, the international deposition organization, under acceptance No. FERM BP-6378 on May 25, 1998. An antibody produced by the hybridoma HSL2 is called HSL2 antibody.

By the same procedure, an antibody which recognizes a human pre-B cell receptor, especially, λ5, was prepared. The hybridoma producing this antibody was named HSL11. An antibody produced by this hybridoma is called HSL11 antibody.

Mass production of HSL2 antibody was performed in the same way as in item 4. of Example 1. The subclass of this antibody was confirmed to be IgG$_1$κ with the use of a monoclonal mouse Ig isotyping kit (Becton Dickinson-Farmingene).

Example 3

Confirmation of Antibody Specificity 1-ELISA

Under the same condition as the ELISA condition 2, the following samples were each reacted with each of the following coated antigen proteins, and the absorbances at 405 nm were measured.

Coated antigen proteins:

① A 10-fold concentrate of the culture supernatant of Ltk$^-$17–72 (pre-B cell receptor)

② Human IgM (human μ chain and human κ chain) (10 μg/ml)

③ Human IgM (human μ chain and human λ chain) (10 μg/ml)

Samples:

① Culture supernatant of hybridoma HSL2 (HSL2 antibody)

② Culture supernatant of hybridoma HSL96 (HSL96 antibody)

③ Culture supernatant of hybridoma HSL11 (HSL11 antibody)

④ Culture supernatant of mouse hybridoma 141PF11 (anti-human κ chain antibody)

⑤ Culture supernatant of mouse hybridoma HP6054 (anti-human λ chain antibody)

Figure 3C:
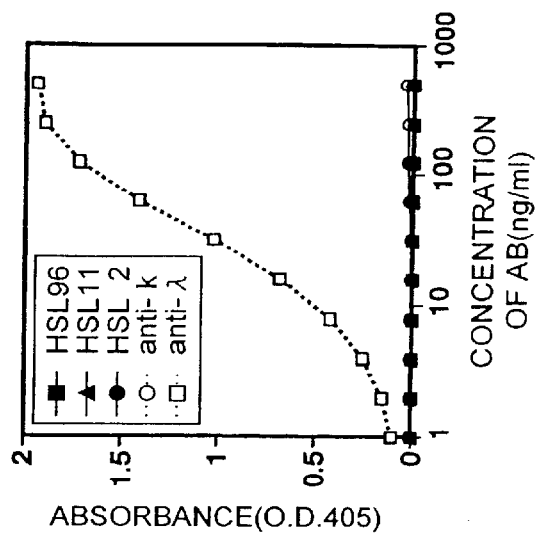
FIG. 3C is a view showing the results of ELISA of HSL2 antibody and HSL96 antibody of the present invention, HSL11 antibody, anti-human κ chain antibody and anti-human λ chain antibody against human IgM (human μ chain and human λ chain), respectively.
Figure 3B:
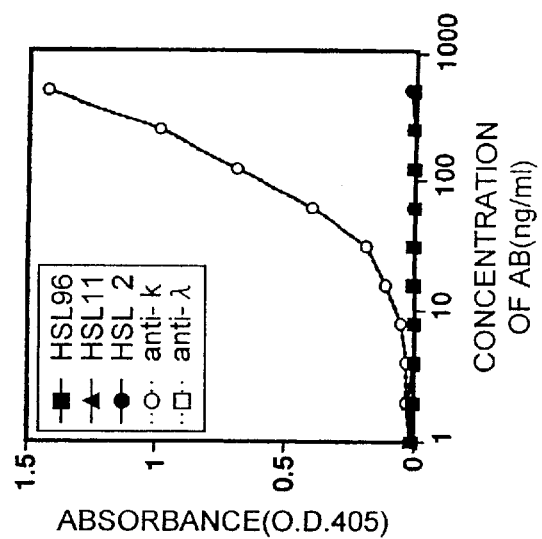
FIG. 3B is a view showing the results of ELISA of HSL2 antibody and HSL96 antibody of the present invention, HSL11 antibody, anti-human κ chain antibody and anti-human λ chain antibody against human IgM (human μ chain and human κ chain), respectively.
Figure 3A:
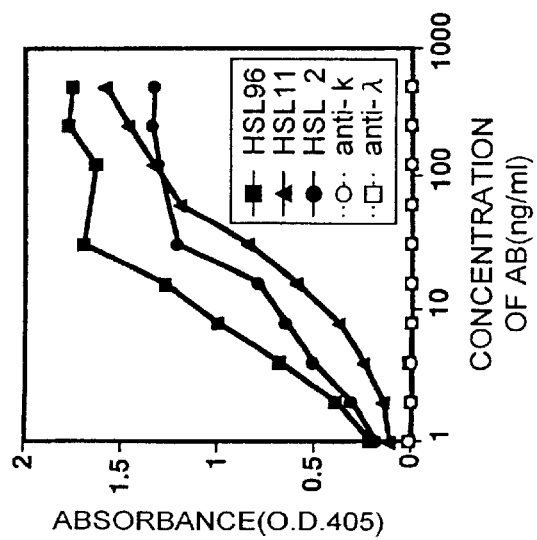
FIG. 3A is a view showing the results of ELISA of HSL2 antibody and HSL96 antibody of the present invention, HSL11 antibody, anti-human κ chain antibody and anti-human λ chain antibody against a pre-B cell receptor, respectively.
Figure 4A:
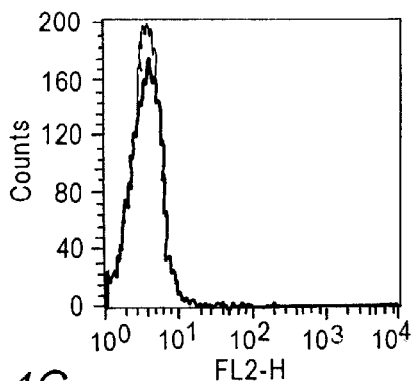
FIG. 4A is a view showing results obtained by immunostaining the cell surface of pro-B cell (RS4;11) with HSL2 antibody (anti-pre-BCR) and analyzing the stained sample with FACS.
Figure 4B:
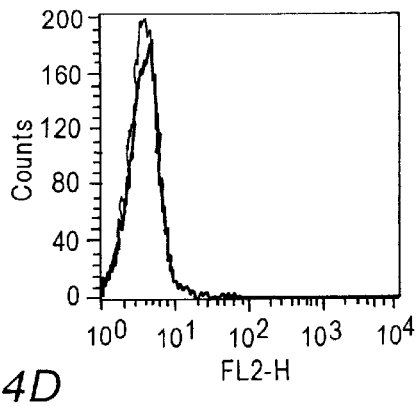
FIG. 4B is a view showing results obtained by immunostaining the cell surface of the pro-B cell with HSL96 antibody (anti-vpreB) and analyzing the stained sample with FACS.
Figure 4C:
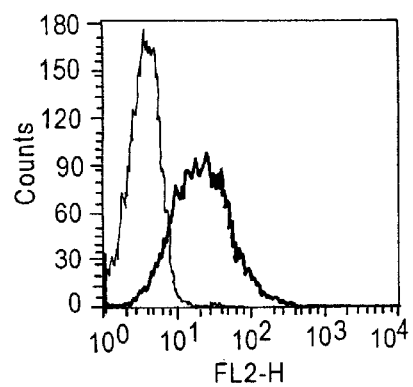
FIG. 4C is a view showing results obtained by immunostaining the cell surface of pre-B cell (697) with HSL2 antibody and analyzing the stained sample with FACS.
Figure 4D:
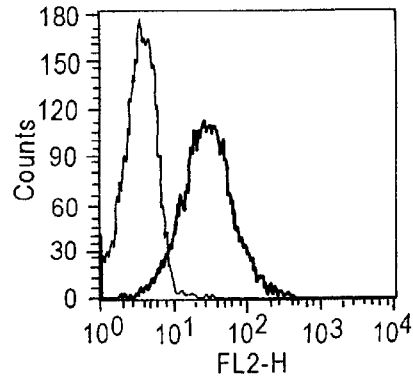
FIG. 4D is a view showing results obtained by immunostaining the cell surface of the pre-B cell with HSL96 antibody and analyzing the stained sample with FACS.
Figure 4E:
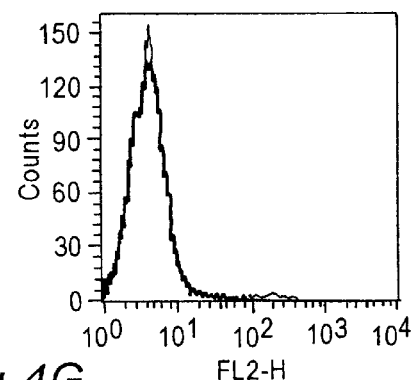
FIG. 4E is a view showing results obtained by immunostaining the cell surface of mature B cell (LBW-4) with HSL2 antibody and analyzing the stained sample with FACS.
Figure 4F:
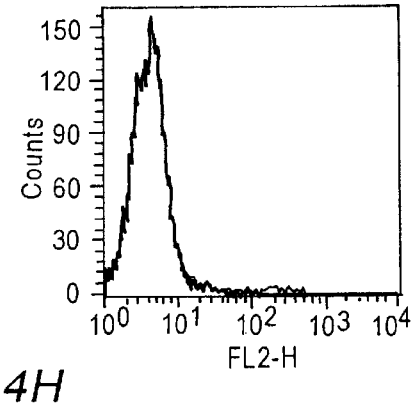
FIG. 4F is a view showing results obtained by immunostaining the cell surface of the mature B cell with HSL96 antibody and analyzing the stained sample with FACS.
Figure 4G:
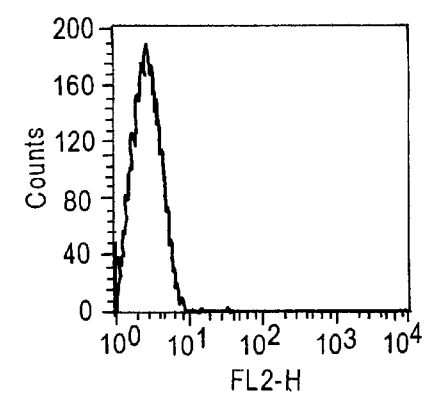
FIG. 4G is a view showing results obtained by immunostaining the cell surface of T cell (Jurkat) with HSL2 antibody and analyzing the stained sample with FACS.
Figure 4H:
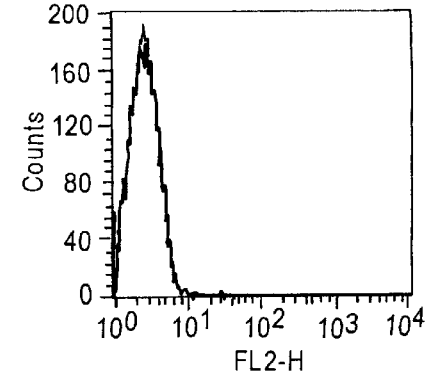
FIG. 4H is a view showing results obtained by immunostaining the cell surface of the T cell with HSL96 antibody and analyzing the stained sample with FACS.
Figure 5A:
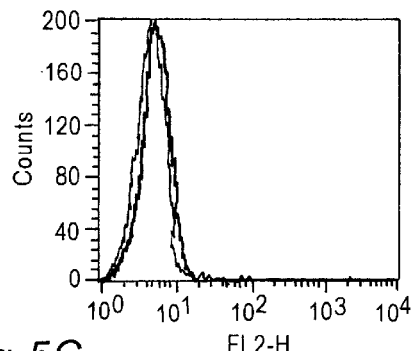
FIG. 5A is a view showing results obtained by immunostaining the cytoplasm of pro-B cell (RS4;11) with HSL2 antibody (anti-pre-BCR) and analyzing the stained sample with FACS.
Figure 5B:
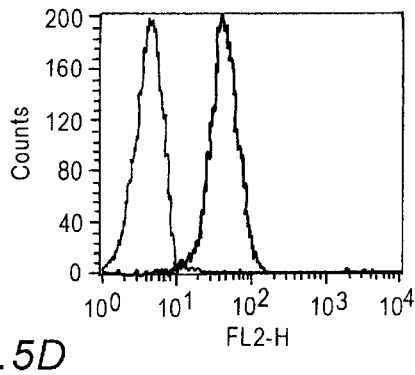
FIG. 5B is a view showing results obtained by immunostaining the cytoplasm of the pro-B cell with HSL96 antibody (anti-VpreB) and analyzing the stained sample with FACS.
Figure 5C:
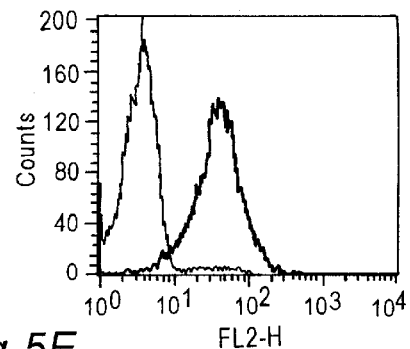
FIG. 5C is a view showing results obtained by immunostaining the cytoplasm of pre-B cell (697) with HSL2 antibody and analyzing the stained sample with FACS.
Figure 5D:
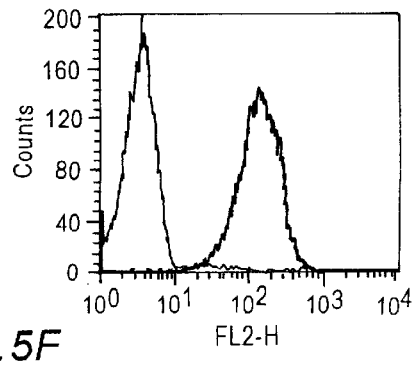
FIG. 5D is a view showing results obtained by immunostaining the cytoplasm of the pre-B cell with HSL96 antibody and analyzing the stained sample with FACS.
Figure 5E:
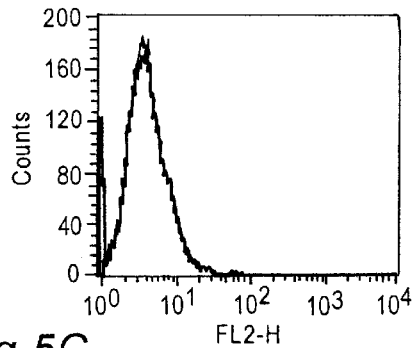
FIG. 5E is a view showing results obtained by immunostaining the cytoplasm of mature B cell (LBW-4) with HSL2 antibody and analyzing the stained sample with FACS.
Figure 5F:
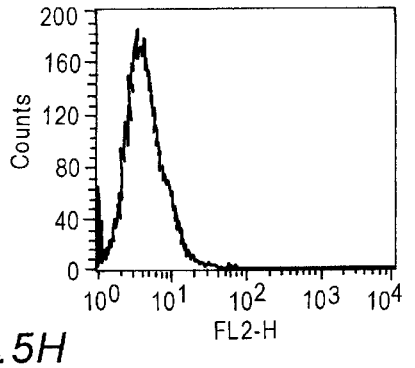
FIG. 5F is a view showing results obtained by immunostaining the cytoplasm of the mature B cell with HSL96 antibody and analyzing the stained sample with FACS.
Figure 5G:
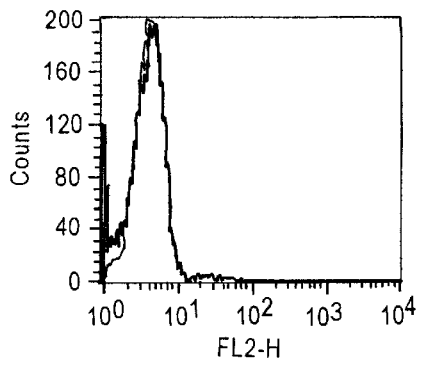
FIG. 5G is a view showing results obtained by immunostaining the cytoplasm of T cell (Jurkat) with HSL2 antibody and analyzing the stained sample with FACS.
Figure 5H:
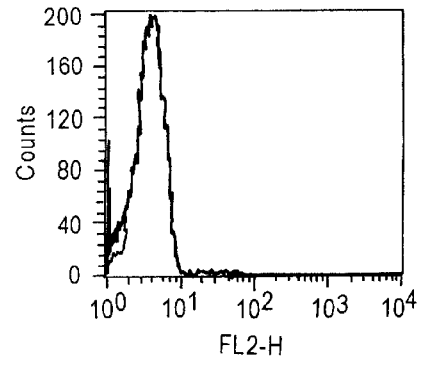
FIG. 5H is a view showing results obtained by immunostaining the cytoplasm of the T cell with HSL96 antibody and analyzing the stained sample with FACS.
Figure 6A:
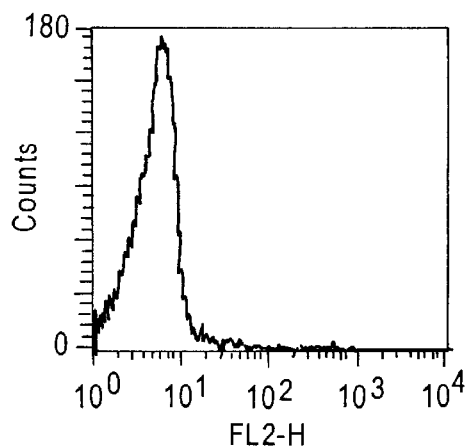
FIG. 6A is a view showing results obtained by immunostaining a transformant (X63/λ5), in which a human λ5 gene has been introduced, with HSL2 antibody (anti-pre-BCR) and analyzing the stained sample with FACS.
Figure 6B:
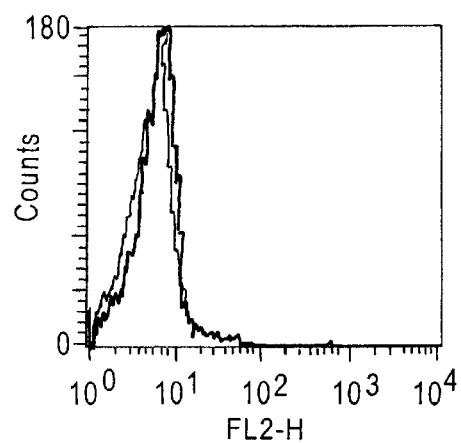
FIG. 6B is a view showing results obtained by immunostaining the transformant, in which a human λ5 gene has been introduced, with HSL96 antibody (anti-VpreB) and analyzing the stained sample with FACS.
Figure 6C:
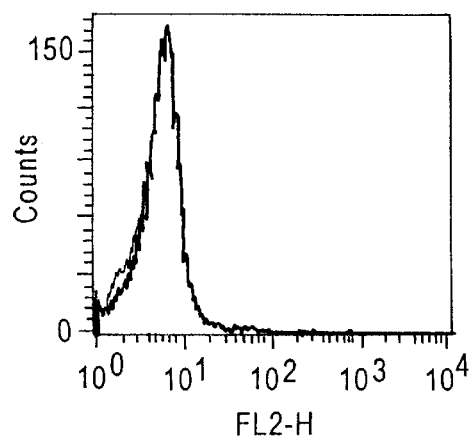
FIG. 6C is a view showing results obtained by immunostaining a transformant (X63/VpreB), in which a human VpreB gene has been introduced, with the HSL2 antibody of the present invention and analyzing the stained sample with FACS.
Figure 6D:
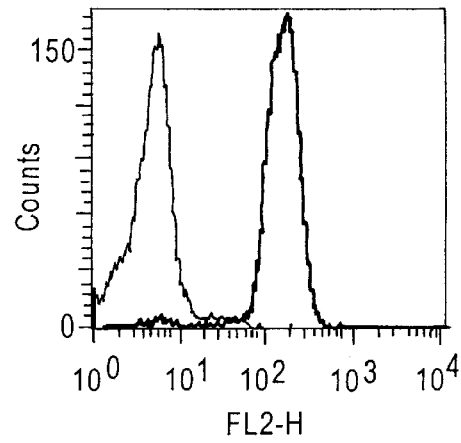
FIG. 6D is a view showing results obtained by immunostaining the transformant, in which a human vpreB gene has been introduced, with HSL96 antibody and analyzing the stained sample with FACS.

Detection Antibody:

A 1:500 dilution of alkaline phosphatase-labeled goat a anti-mouse IgG antibody
Substrate: PNPP The results are shown in FIGS. 3A to 3C. HSL2 antibody was found to recognize the pre-B cell receptor, and not to react with human $\mu$ chain, $\kappa$ chain, or $\lambda$ chain. Therefore, the $\mu$ chain of the human pre-B cell receptor is not the only portion that HSL2 antibody recognizes. It was also found that HSL96 did not react with human $\mu$ chain, $\kappa$ chain, or $\lambda$ chain.

Example 4

Confirmation of Antibody Specificity 2—FACS

1. Immunostaining of Cell Surface

The following cell strains were each reacted with HSL2 antibody or HSL96 antibody for staining of the cell surface, followed by measurement with FACS Calibur (Becton Dickinson).

Cell strains:
① Pro-B leukemia cell line RS4;11
② Pre-B leukemia cell line 697
③ Mature B cell line LBW-4
④ T cell line Jurkat Specifically, cells of each strain washed twice with 0.1% BSA-PBS were suspended in a 0.1% BSA-PBS buffer to a cell count of $2\times10^7$/ml, and the suspension was allowed to stand for 10 minutes on ice. The cells were taken in an amount of 50 $\mu$l ($1\times10^6$) into each well of a 96-well plate. To each well, 100 $\mu$l of biotin-labeled HSL2 antibody or biotin-labeled HSL96 antibody (concentration 1 $\mu$g/ml) was added, followed by performing reaction for 30 minutes at room temperature. Then, 100 $\mu$l of PE-labeled streptoavidin (2 $\mu$g/ml) was added to each well for color development.

This sample was measured with FACS Calibur (Becton Dickinson).

The results are shown in FIGS. 4A to 4H. In cell surface staining, it was confirmed that pre-B leukemia cells are immunologically stained with HSL2 antibody or HSL96 antibody, while the pro-B leukemia cell line, mature B cell line, or T leukemia cell line was not immunostained with HSL2.

2. Cytoplasmic Immunostaining

In the same manner as in the aforementioned cell surface staining, cytoplasmic staining was performed using 0.1% BSA-0.05% saponin-10) mM Hepes (pH 7.3)-PBS as a buffer for suspending the cells and the antibody. Measurement with FACS Calibur was performed.

The results are shown in FIGS. 5A to 5H. It was confirmed that the pre-B leukemia cell strain is cytoplasmic stained with HSL2 antibody, while the pro-B cell line, mature B cell line, or T cell line is not intracellularly immunostained with HSL2 antibody. HSL96 antibody was confirmed to immunostain pro-B leukemia cell in cytoplasmic staining. Thus, HSL2 antibody and HSL96 antibody exhibit different effects in the cytoplasmic staining of pro-B cells.

3. Cytoplasmic Staining of Transformant X63-Ag8.653

The human $\lambda 5$ gene or human VpreB gene prepared in the aforementioned item 1 of Example 1 was introduced into mouse myeloma X63-Ag8.653 (J. Immunol., Vol. 123, page 1548) by electroporation in the following two ways to construct transformants:

① Introduction of only $\lambda 5$ (X63/$\lambda 5$)
② Introduction of only VpreB (X63/VpreB)

Each of these transformants was subjected to cytoplasmic staining using saponin buffer in the aforementioned manner, and measured with FACS Calibur.

The results are shown in FIGS. 6A to 6D. HSL2 antibody was confirmed to react with neither the recombinant VpreB molecule nor the recombinant $\lambda 5$ molecule, whereas HSL96 antibody was confirmed to react with the recombinant VpreB molecule, but not with the recombinant $\lambda 5$ molecule.

Example 5

Confirmation of Antibody Specificity 3—Immunoprecipitation

A culture supernatant (1 ml) of hybridoma HSL2 was mixed overnight with 20 $\mu$l of protein G Sepharose (Pharmacia) at a ratio of 50% V/V at 4° C.

The mixture was centrifuged for 5 minutes at 10,000 rpm to separate the antibody-bound protein G Sepharose.

The protein G Sepharose was washed with a solvent (1% NP-40, 150 mM NaCl).

Pre-B leukemia cell line Nalm6 cells or pro-B cell line RS4;11 cells ($1\times10^5$) intracellularly labeled with isotope $^{35}$S methionine/cysteine, and a solvent (1% NP-40, 150 mM NaCl) were mixed to obtain a cell solution.

The antibody-bound protein G Sepharose was suspended in the cell solution, and mixed for 2 hours.

Separately, the above culture supernatant was reacted with each of the two types of X63-Ag8.653 transformants prepared in Example 2.

The above mixture was centrifuged for 5 minutes at 10,000 rpm to separate an immunoprecipitate (Nalm6-derived protein bound to the protein G Sepharose).

For comparison, the following antibodies were used:
① HSL11 antibody (antibody which recognizes $\lambda 5$ of human pre-B cell receptor)
② HSL96 antibody (antibody which recognizes VpreB of human pre-B cell receptor)
③ Control (mouse IgG$_1\kappa$)
④ Anti-human $\mu$ chain antibody (only for immunoprecipitation of cell solution)

Washing of the immunoprecipitate with about 1 ml of a washing solution (1% NP-40, 650 mM NaCl) was repeated 4 times to obtain the immunoprecipitate as a sample for electrophoresis.

The immunoprecipitate was reduced for 5 minutes at 95° C. in the presence of 2-mercaptoethanol, and electrophoresed on 13% SDS polyacrylamide gel.

Figure 7:
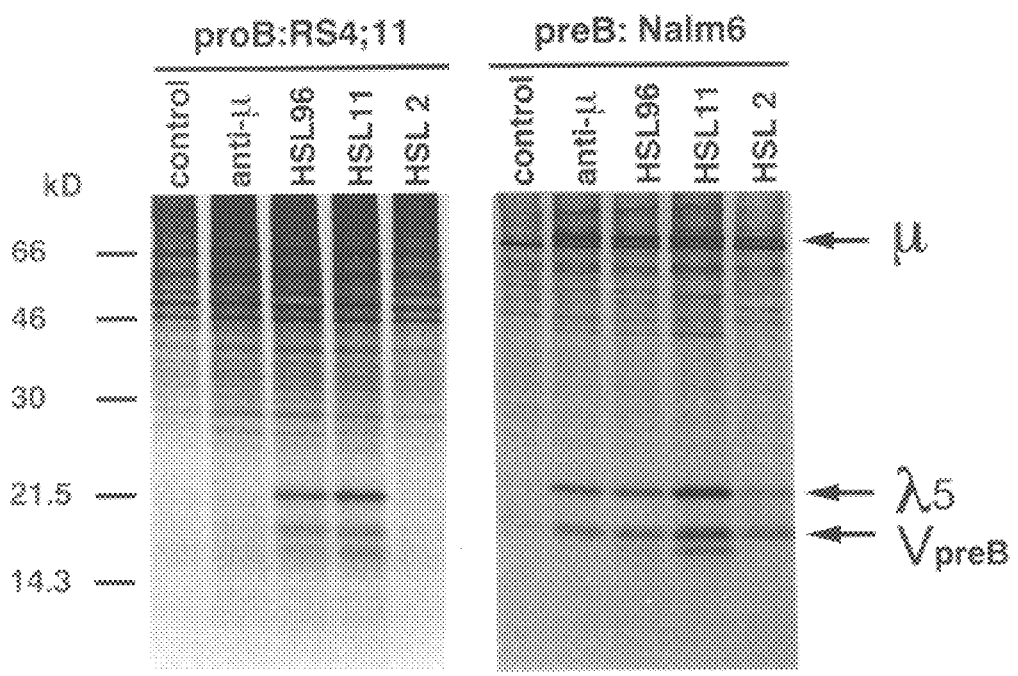
FIG. 7 is an electrophoretic photograph showing the results of electrophoresis of immunoprecipitates obtained by immunoprecipitation of human pre-B cell and human pro-B cell with the use of the HSL2 antibody of the present invention, and HSL96 antibody, HSL11 antibody, anti-human μ chain antibody and mouse $IgG_1κ$ as comparative antibodies.
Figure 8:
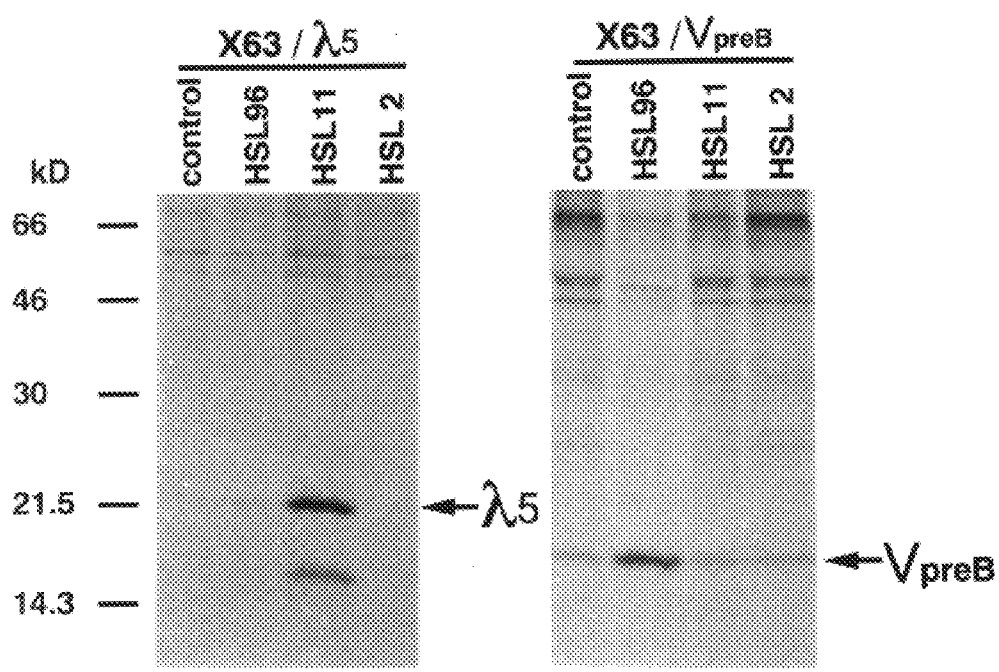
FIG. 8 is an electrophoretic photograph showing the results of electrophoresis of immunoprecipitates obtained by immunoprecipitation of a transformant having a human λ5 gene introduced therein, a transformant having a human VpreB gene introduced therein and human pre-B cells with the use of the HSL2 antibody of the present invention, and HSL96 antibody, HSL11 antibody, and mouse $IgG_1κ$ as comparative antibodies.

The results are shown in FIGS. 7 and 8.

The right half of FIG. 7 shows the results of immunoprecipitation of the cell solution of pre-B leukemia cell line Nalm6 with each antibody. The lanes show, from right to left, the results of immunoprecipitation with HSL2 antibody, HSL11 antibody, HSL96 antibody, anti-human $\mu$ chain antibody, and control (mouse IgG$_1\kappa$). Upon immunoprecipitation with HSL2 antibody or HSL96 antibody, bands for $\lambda 5$, VpreB and $\mu$ chain appeared, thus confirming that the pre-B cell receptor is immunoprecipitated with HSL2 antibody.

The left half of FIG. 7 shows the results of immunoprecipitation of the cell solution of pro-B leukemia cell line RS4;11 with each antibody. The lanes show, from right to left, the results of immunoprecipitation with HSL2 antibody, HSL11 antibody, HSL96 antibody, anti-human $\mu$ chain antibody, and control (mouse IgG$_1\kappa$). The left-end lane represents markers. The lane for HSL2 antibody showed no bands for $\lambda 5$ or vpreB, thus confirming that the pro-B cell receptor is not immunoprecipitated with HSL2 antibody.

The left half of FIG. 8 shows the results of immunoprecipitation of recombinant $\lambda 5$ with each antibody. The lanes show, from right to left, the results of immunoprecipitation with HSL2 antibody, HSL11 antibody, HSL96 antibody, and control (mouse IgG$_1$κ). The lane for HSL2 antibody or HSL96 antibody showed no band for λ5, thus confirming that λ5 is not immunoprecipitated with HSL2 antibody or HSL96 antibody.

The right half of FIG. 8 shows the results of immunoprecipitation of recombinant vpreB with each antibody. The lanes show, from right to left, the results of immunoprecipitation with HSL2 antibody, HSL11 antibody, HSL96 antibody, and control (mouse IgG$_1$κ). The lane for HSL2 antibody showed no band for VpreB, thus confirming that VpreB is not immunoprecipitated with HSL2 antibody. The lane for HSL96 antibody showed a band for VpreB.

Example 6

Figure 9:
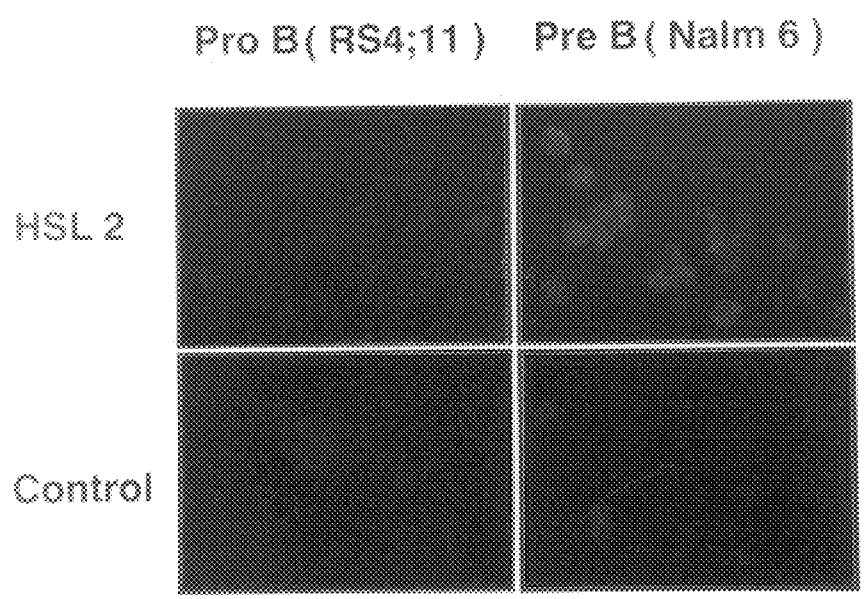
FIG. 9 is a micrograph showing results obtained by reacting each of the pre-B leukemia cell line Nalm6 and the pro-B leukemia cell line RS4;11 with HSL2 antibody to perform immunostaining of the cytoplasm of the cells, followed by color development with the use of FITC.

Microscopic Observation of Immunostained cells
1. Microscopic Observation of Immunostained pre-B Cells Pre-B leukemia cell line Nalm6 and pro-B leukemia cell line RS4;11 were each reacted with biotin-labeled HSL2 in the same manner as in item 1. of Example 4 to perform immunostaining intracellularly. FITC-labeled streptoavidin was reacted with the biotin-labeled HSL2, and its fluorescence was observed under a fluorescence microscope. The results are shown in FIG. 9. Fluorescence was observed for pre-B cell line Nalm6, but not for pro-B cell line RS4;11. This finding confirms that microscopic observation of an intracellular immunostaining image obtained by reaction with HSL2 antibody can easily distinguish between pre-B cells and pro-B cells, and can detect only pre-B cells.

Upon staining of the cell surface, fluorescence was similarly observed only for pre-B cells by use of HSL2 antibody. This staining was confirmed to be capable of detecting pre-B cells alone.

Example 7

Figure 10:
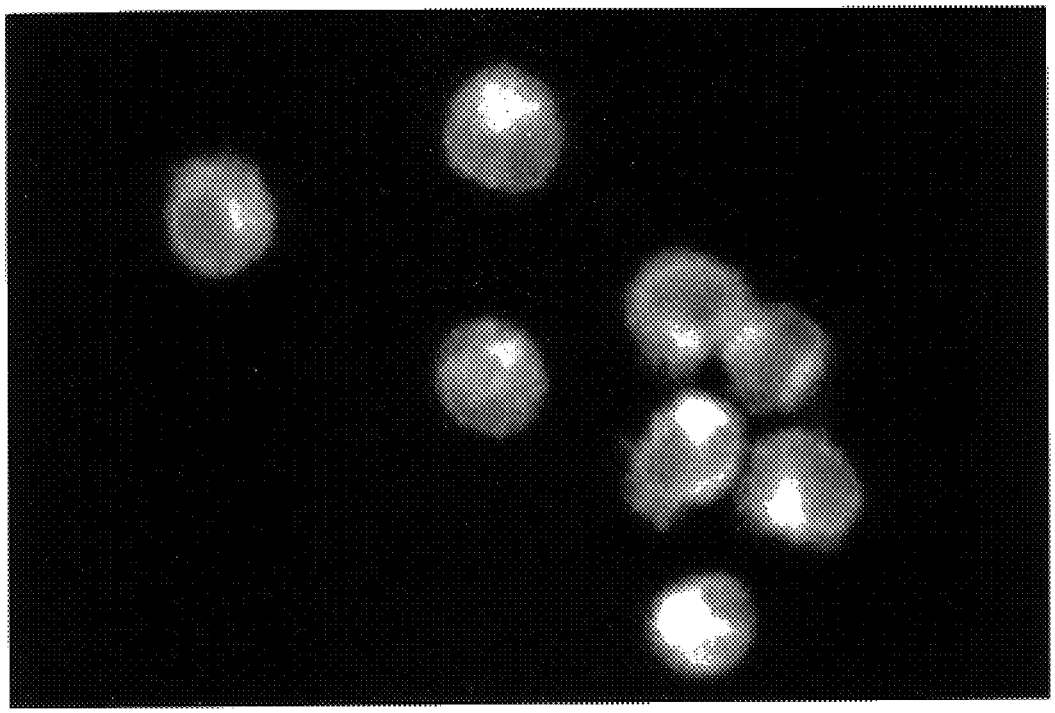
FIG. 10 is a micrograph showing results obtained by reacting the pre-B leukemia cell line Nalm6 with HSL96 antibody to perform immunostaining of the cytoplasm of the cells, followed by color development with the use of FITC.

Microscopic Observation of Immunostained cells
1. Microscopic Observation of Immunostained pre-B Cells Pre-B leukemia cell line Nalm6 was reacted with biotin-labeled HSL96 antibody in the same manner as in item 1. of Example 4 to perform immunostaining intracellularly. FITC-labeled streptoavidin was reacted with the biotin-labeled HSL96 antibody, and its fluorescence was observed under a fluorescence microscope. The results are shown in FIG. 10. Cells showing FITC fluorescence are Nalm6. This finding confirms that microscopic observation of an intracellular immunostaining image obtained by reaction with HSL96 can easily detect pre-B cells.

2. Microscopic Observation of Immunostained pro-B Cells

Figure 11A:
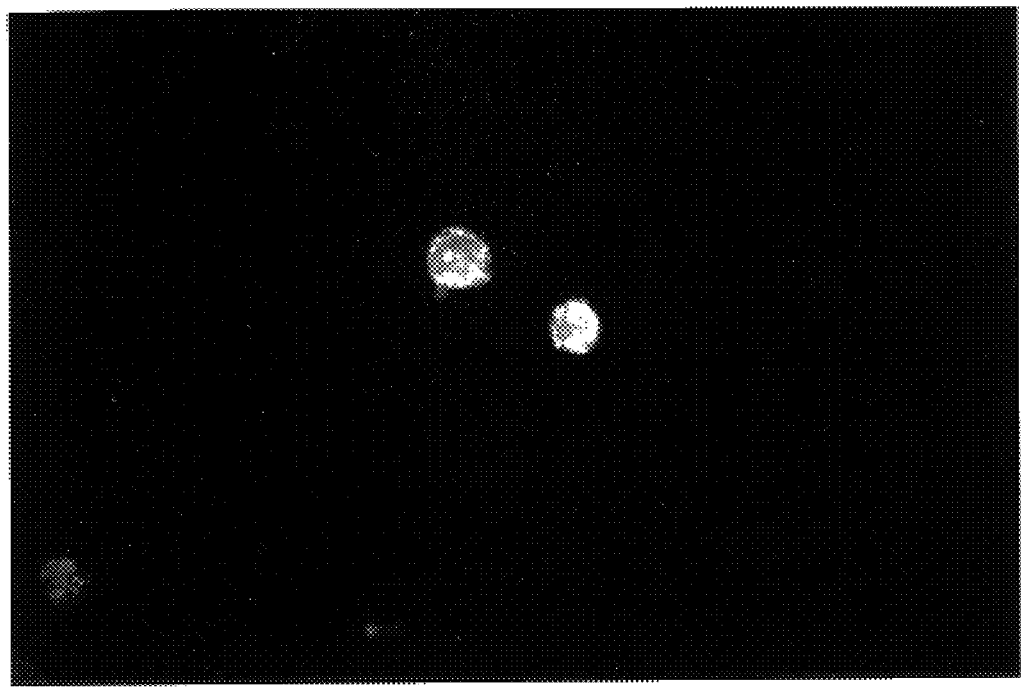
FIG. 11A is a micrograph showing results obtained by reacting the pro-B leukemia cell line Nalm27 with HSL96 antibody with the use of saponin buffer to perform immunostaining of the cytoplasm of the cells, followed by color development with the use of FITC (results obtained by reaction with HSL96 antibody)
Figure 11B:
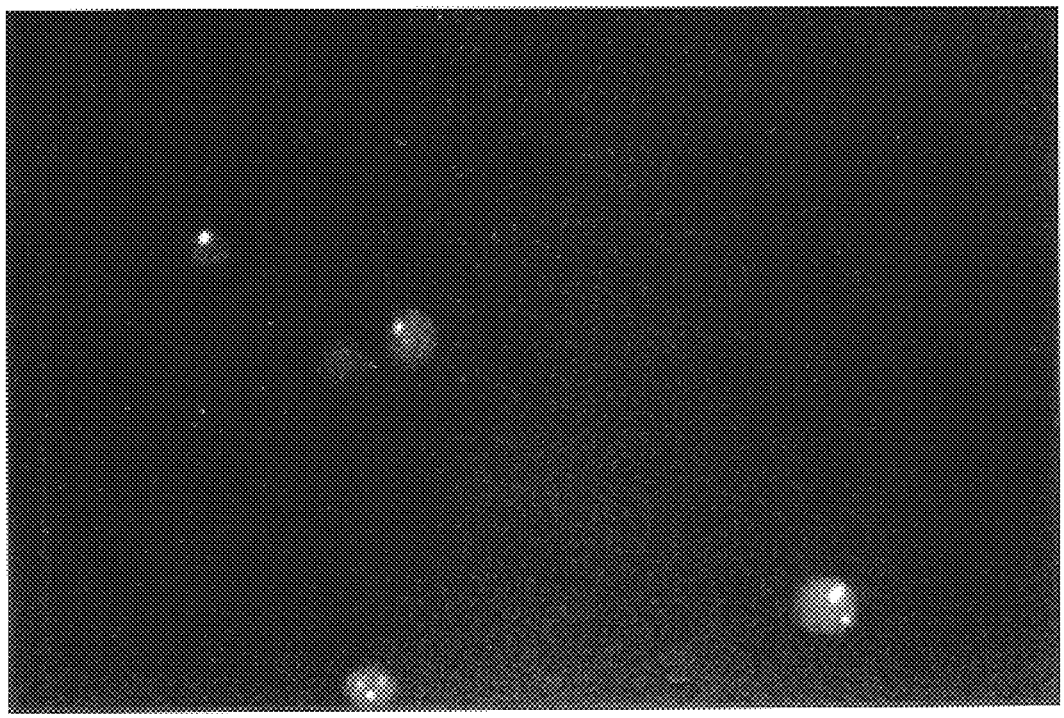
FIG. 11B is a micrograph showing results obtained by reacting the pro-B leukemia cell line Nalm27 with HSL96 antibody with the use of saponin buffer to perform immunostaining of the cytoplasm of the cells, followed by color development with the use of FITC (results obtained by reaction with mouse $IgG_1κ$ as a control).

Pro-B leukemia cell line Nalm27 was reacted with biotin-labeled HSL96 antibody and saponin buffer in the same manner as in item 2. of Example 3 to perform immunostaining intracellularly. FITC-labeled streptoavidin was reacted with the biotin-labeled HSL96 antibody, and its fluorescence was observed under a fluorescence microscope. The results are shown in FIG. 11. FIG. 11A is a micrograph of the results of reaction with HSL96 antibody, while FIG. 11B is a micrograph of the results of reaction with IgG$_1$κ used as a control instead of HSL96 antibody. Cells showing FITC fluorescence are Nalm27. The results confirm that microscopic observation of an intracellular immunostaining image obtained by reaction between HSL96 antibody and pro-B cells can easily detect pro-B cells.

The results of specificity studies in the aforementioned Examples 3 to 5 are summarized in Table 2, together with the specificities of the antibodies shown in Table 1. The reaction site for the existing antibodies of prior arts is only λ5 or only VpreB, and the antibody that recognizes a complex of human μ chain, human λ5 and human VpreB is HSL2 only.

TABLE 2

| | | Cell surface staining (FACS) | | Cytoplasmic staining (FACS) | | | | |
|---|---|---|---|---|---|---|---|---|
| Antibody | Immunogen | Pro-B cell | Pre-B cell | Pro-B cell | Pre-B cell | Reaction site | Immunoprecipitation | Isotype |
| HSL2 | Pre-B cell receptor (mouse μ chain + human SL chain) | Negative | Positive | Negative | Positive | Pre-B cell receptor | Pre-B cell receptor | IgG |
| HSL96 | Pre-B cell receptor (mouse μ chain + human SL chain) | Negative | Positive | Positive | Positive | VpreB (does react with λ5) | VpreB | IgG |
| SLC1 | Pre-B cell receptor (human μ chain + human SL chain) | Negative | Positive | No data | No data | λ5 | No data | IgG |
| SLC2 | Pre-B cell receptor (human μ chain + human SL chain) | Negative | Positive | No data | No data | λ5 | No data | IgM |
| SLC3 | Pre-B cell receptor (human μ chain + human SL chain) | Negative | Positive | No data | No data | λ5 | No data | IgM |
| SLC4 | Pre-B cell receptor (human μ chain + human SL chain) | Negative | Positive | No data | No data | λ5 | No data | IgG |
| 9C2 | Part of synthetic VpreB molecule | Very weakly positive | Positive | No data | No data | VpreB | No data | IgM |
| 3C7 | Recombinant VpreB | Positive | Very weakly positive | No data | No data | VpreB | No data | IgM |
| 6F6 | Recombinant VpreB | Positive | Very weakly positive | No data | No data | VpreB | No data | IgM |
| B-MAD176 | Recombinant VpreB | Negative | Positive | No data | No data | No data | No data | IgM |

TABLE 2-continued

| Antibody | Immunogen | Cell surface staining (FACS) | | Cytoplasmic staining (FACS) | | Reaction site | Immunoprecipitation | Isotype |
| --- | --- | --- | --- | --- | --- | --- | --- | --- |
| | | Pro-B cell | Pre-B cell | Pro-B cell | Pre-B cell | | | |
| B-MAD688 | Recombinant VpreB | Positive | Positive | No data | No data | VpreB | SH chain (only when formed as complex with SL chain) | IgM |
| B-MAD792 | Recombinant VpreB | Negative | Positive | No data | No data | No data | No data | IgM |
| B-MAD1112 | Recombinant VpreB | Positive depending on cell strain | Positive | No data | No data | VpreB | No data | IgM |

The HSL2 of the present invention was found not to recognize any of human μ chain, human λ5 and human VpreB existing alone, but found to recognize a pre-B cell receptor formed by association of human μ chain, human λ5 and human VpreB. That is, the stereostructure of the pre-B cell receptor was found to be a prerequisite for recognition of the pre-B cell receptor by HSL2 antibody.

The HSL96 antibody of the present invention has been ascertained to react with a recombinant VpreB molecule present alone. Thus, this antibody is presumed to have reacted with a VpreB molecule intracellularly in pro-B cells.

The HSL96 of the present invention is capable of intracellular staining for each of pre-B cell and pro-B cell. Conventional antibodies are lacking in such a finding.

As shown in Example 7, the HSL96 antibody of the present invention permits immunostained cells to be observed microscopically. Conventional antibodies are lacking in such a finding.

The antibodies of the present invention make it possible to detect human pro-B cells and human pre-B cells from among human lymphocytes.

When the surface or cytoplasm of a cell is found to have been stained with one of the antibodies of the present invention which antibody recognizes a human pre-B cell, but does not recognize a pro-B cell, this cell can be identified as a human pre-B cell. If a cell is not stained with this antibody, but stained with the other antibody, this cell can be defined as a pro-B cell. The antibody of the invention which recognizes VpreB reacts with VpreB of the surrogate light chain of a human pre-B cell receptor, but does not react with λ5. Since VpreB corresponds to the variable region of the light chain, and λ5 corresponds to the constant region, the antibody of the present invention has high specificity among antibodies reactive with a human pre-B cell.

Lymphocytes are separated from a blood sample or a bone marrow sample of a patient suspected of having acute lymphoblastic leukemia in childhood. The cell surface or cytoplasm of the lymphocytes is immunostained with a combination of the antibodies of the present invention, and observed by means of FACS Calibur. If stained cells are observed at that time, these cells can be identified as human pre-B cells or pro-B cells. The patient can be diagnosed as suffering from leukemia due to abnormal proliferation of human pre-B cells or abnormal proliferation of human pro-B cells. Conventional technologies have been unable to specify which stage of differentiation of B cells the acute lymphoblastic leukemia in childhood at issue comes from. The antibodies of the present invention can determine this.

More particularly, the combined use of the following antibodies of the present invention, (1) an antibody which recognizes a human pre-B cell receptor, and does not recognize a human pro-B cell, (2) an antibody which recognizes a VpreB molecule, (3) an antibody which recognizes a λ5 molecule, and (4) an antibody which recognizes a B cell, can lead to a diagnosis of which differentiation stage of B cells the acute lymphoblastic leukemia in childhood at issue results from. For example, when a sample is reacted with each of the antibodies (1) to (4), and only the antibody (1) has stained the sample, a patient giving the sample is found to have leukemia due to pre-B cells. If only the antibody (2) has stained the sample, the patient presenting the sample is found to have leukemia due to pro-B cells.

Intracellular staining using saponin buffer on this occasion permits easier measurement with FACS Calibur, and accordingly, easier diagnosis than before can be performed.

The antibodies of the present invention are also applicable when immunostained cells are observed under a microscope.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An anti-human pre-B cell receptor monoclonal antibody produced by hybridoma HSL2 (originally deposited with National Institute of Bioscience and Human Technology, Agency of Industrial Science and Technology, Ministry of Industrial Trade and Industry 1–3, Higashi 1-chome, Tsukuba-shi, Ibaraki-ken, Japan, on Oct. 16, 1997 under acceptance No. FERM-P16476; and transferred to the international deposition organization, National Institute of Bioscience and Human Technology, Agency of Industrial Science and Technology, Ministry of Industrial Trade and Industry, 1–3, Higashi 1-chome, Tsukuba-shi, Ibaraki-ken, Japan, on May 25, 1998 under acceptance No. FERM-BP6378), or an antigen-binding fragment of the monoclonal antibody.

2. A monoclonal antibody produced by hybridoma HSL96 (originally deposited with National Institute of Bioscience and Human Technology, Agency of Industrial Science and Technology, Ministry of Industrial Trade and Industry, 1–3, Higashi 1-chome, Tsukuba-shi, Ibaraki-ken, Japan, on May 30, 1997 under acceptance no. FERM-P16251; and transferred to the international deposition organization, National Institute of Bioscience and Human Technology, Agency of Industrial Science and Technology, Ministry of Industrial Trade and Industry, 1–3, Higashi 1-chome, Tsukuba-shi, Ibaraki-ken, Japan, on May 25, 1998 under acceptance no. FERM-BP6375), or an antigen-binding fragment of the monoclonal antibody.

3. A method for detecting a human pro-B cell, which comprises (i) contacting the antibody or its antigen-binding fragment according to claim 2 with a sample believed to contain human pro-B cell and a saponin buffer, and (ii) detecting the presence of said human pro-B cell by differential staining.

* * * * *

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1

-continued

```
ggaactcgag ccacaaggac ctctgaccct                               30

<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
ggaagcggcc gcaggccttt gggtggggtc gg                            32

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
ggaactcgag ggagtcagag ctctgcatgt                               30

<210> SEQ ID NO 4
<211> LENGTH: 32
<212> TYPE: DNA
<213> ORGANISM: Artificial Sequence
<220> FEATURE:
<223> OTHER INFORMATION: Primer

<400> SEQUENCE: 4
ggaagcggcc gcaggggatg cgtgcctctg ct                            32
```